United States Patent [19]

Nestor et al.

[11] Patent Number: 4,698,442

[45] Date of Patent: Oct. 6, 1987

[54] ω-GUANIDINO-SUBSTITUTED-α-AMINO ACIDS

[75] Inventors: John J. Nestor, San Jose; Brian H. Vickery, Saratoga, both of Calif.

[73] Assignee: Syntex (U.S.A.) Inc., Palo Alto, Calif.

[21] Appl. No.: 874,256

[22] Filed: Jun. 13, 1986

Related U.S. Application Data

[63] Continuation of Ser. No. 607,873, May 7, 1984, abandoned, which is a continuation-in-part of Ser. No. 451,671, Dec. 21, 1982, Pat. No. 4,481,190.

[51] Int. Cl.$^4$ ............................................ C07C 101/04
[52] U.S. Cl. .................................... 562/560; 544/164; 544/297; 548/306; 548/315; 562/439; 562/440; 562/507; 540/605
[58] Field of Search ............... 562/439, 440, 507, 560; 544/122, 139, 332, 164, 297; 548/306, 315; 260/239 BC

[56] References Cited

U.S. PATENT DOCUMENTS

| | | | |
|---|---|---|---|
| 3,824,267 | 7/1974 | Ito ........................................ | 562/560 |
| 3,943,253 | 3/1976 | Barer ................................... | 562/560 |
| 4,499,068 | 2/1985 | Silbering ............................. | 424/52 |

OTHER PUBLICATIONS

Kakimoto, J., Biol. Chem., 245, pp. 5751–5765 (1960).
Patthy, Acta. Biochim. Biophys. Acad. Sci., Hung., 12, pp. 191–196 (1977).
Pundak, J. Org. Chem., 46, pp. 808–809 (1981).

*Primary Examiner*—Michael L. Shippen
*Attorney, Agent, or Firm*—Ellen J. Wise; Tom M. Moran; Alan M. Krubiner

[57] ABSTRACT

α-amino acids having a substituted ω-guanidino group are disclosed herein.

13 Claims, No Drawings

ω-GUANIDINO-SUBSTITUTED-α-AMINO ACIDS

This is a continuation of pending application Ser. No. 607,873, filed May 7, 1984, now abandoned, incorporated herein by reference, which is a continuation-in-part of pending U.S. patent application Ser. No. 451,761 filed Dec. 21, 1982, now U.S. Pat. No. 4,481,190.

BACKGROUND OF THE INVENTION

This invention relates to α-amino acids having an ω-guanidino group wherein at least one of the guanidino nitrogens are substituted. More specifically, this invention covers arginine-type amino acids wherein one or both of the terminal guanidino nitrogens ($H_2N-C=NH$) is substituted.

In 1970, Kakimoto and Akazawa reported the isolation and identification of $N^G,N^{G'}$ and $N^G,N'^G$-dimethyl-arginine from urine. This work was reported in *J. Biol. Chem.*, 245, No. 21, 5751-5765 (1970). Subsequently, Patthy A., et al., reported the preparation and characterization of mono-, di-, and tri-methyl related arginines (*Acta. Biochim. Biophys. Acad. Sci. Hung.*, 12 (3), 191-6 (1977).

It has now been discovered that substituting one or both of the guanidino nitrogens of amino acids such as arginine, homoarginine and related amino acids, provides an amino acyl residue which will increase the activity of a protein into which is incorporated and/or will increase the t ½ of that peptide.

SUMMARY OF THE INVENTION

This invention refers to novel D- or L-ω-guanidino-substituted α-amino acids and amino acyl residues which do not occur in nature. The invention is also directed to various methods of use of these amino acids. A further aspect of the invention involves processes for the preparation of these compounds.

DETAILED DESCRIPTION OF THE INVENTION

Description of the Amino Acids

The present invention relates to D- and L-α-amino acids and their corresponding amino acyl radicals which have the formula $$H_2N-CH-COOH \quad (I)$$
$$|$$
$$(CH_2)_n$$
$$|$$
$$NH$$
$$|$$
$$R_1-C=NR_2$$

and the pharmaceutically acceptable salts thereof wherein n is 1 to 5;

$R_1$ is alkyl of 1-12 carbon atoms, halo lower alkyl or $-NHR_3$ wherein $R_3$ is alkyl of 1-12 carbon atoms, cycloalkyl, phenyl, benzyl, halo lower alkyl, morpholino or $-(CH_2)_nN(R_4)_2$ wherein n is 1-5 and $R_4$ is lower alkyl;

$R_2$ is hydrogen or $R_3$; or $R_1$ and $R_2$ comprise a ring represented by the following structural formulas:

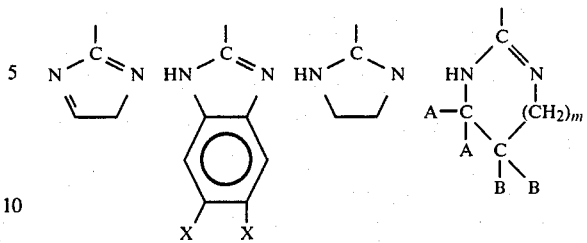

wherein
m is 0-6;
A and B are independently hydrogen, alkyl of 1-6 carbon atoms or cycloalkyl; and
X is halo or A and the pharmaceutically acceptable salts thereof. Compounds wherein n is 3 and $R_1$ is $-NHR_3$ wherein $R_3$ is methyl and $R_2$ is hydrogen or methyl are excluded from this invention.

These amino acids are useful in the preparation of all peptides, polypeptides and proteins.

This invention covers the amino acyl radicals which are derived from formula I. For example, this invention covers the amino acyl radical represented by the structure $$-HN-CH-CO- \quad (IA)$$
$$|$$
$$(CH_2)_n$$
$$|$$
$$NH$$
$$|$$
$$R_1-C=NR_2$$

which would be the form in which formula I would exist when incorporated into a peptide, polypeptide or the like; or when present in a compound which is not a polymer based on α-amino acids. The term "amino acyl radical" also includes the structures derived from formula I wherein either one of the carboxyl or α-amino groups is a radical as represented by formula (IA), i.e. formula I is the C-terminal or N-terminal amino acid of a polypeptide.

As used herein, the term "pharmaceutically acceptable salts" refers to salts which retain the desired biological activity of the parent compound and do not impart any undesired toxicological effects. These salts may be derived from either acid or base.

Examples of acid addition salts formed with inorganic acids or hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, glucuronic acid, citric acid, maleic acid, ascorbic acid, benzoic acid, tannic acid, pamoic acid, alginic acid, polyglutamic acid, naphthalene sulfonic acid, and the like.

Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, cyclohexylamine, t-butylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, cyclohexylamine, t-butylamine, choline and caffeine.

The term "lower alkyl" refers to a straight or branched chain saturated hydrocarbon group having from 1–4 carbon atoms such as, for example, methyl, ethyl n-propyl, isopropyl, n-butyl, isobutyl, sec-butyl and tert-butyl. "Halo lower alkyl" refers to a lower alkyl radical substituted with halo groups, especially those having one, two or three halo groups on the ω-carbon. The halo group may be fluoro, chloro or bromo. This group is exemplified by trifluoromethyl, trifluoroethyl, trifluoropropyl, trichloroethyl and the like.

"Alkyl of 1–6 carbon atoms" encompasses the same substituents as lower alkyl but in addition may have 5 or 6 carbon atoms such as, for example, a n-pentyl, n-hexyl or other branched 5 or 6 carbon membered moiety.

"Alkyl of 1–12 carbon atoms" comprises a radical of 1–12 carbon atoms and hydrogen only, as noted above for lower alkyl, except that the radical may have up to 12 carbon atoms.

The term "cycloalkyl" refers to a cyclic saturated hydrocarbon group having from 3–6 carbon atoms, for example, cyclopropyl, cyclobutyl, cyclopentyl and cyclohexyl.

PREFERRED EMBODIMENTS OF THE INVENTION

The preferred compounds of the present invention are the compound of formula I wherein n is 2–4, $R_1$ is —$NHR_3$ wherein $R_3$ is alkyl of 2–6 carbon atoms, cycloalkyl, phenyl, benzyl or halo lower alkyl and $R_2$ is hydrogen, alkyl of 2–6 carbon atoms, phenyl, benzyl or halo lower alkyl or $R_1$ and $R_2$ comprise a ring represented by the following structural formula:

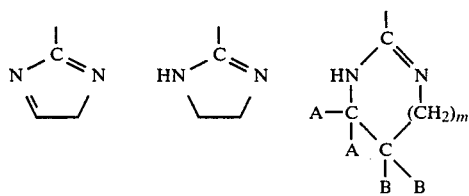

wherein m is 0–2 and A and B are hydrogen or alkyl of 1–4 carbon atoms.

More preferred are those compounds wherein n is 3 or 4, $R_1$ is —$NHR_3$ wherein $R_3$ is alkyl of 2–6 carbon atoms and $R_2$ is alkyl of 2–6 carbon atoms. Most preferred are those compounds wherein n is 3, $R_1$ is —$NHR_3$ wherein $R_3$ is ethyl, isopropyl, n-propyl, n-butyl, hexyl, or cyclohexyl and $R_2$ is the same as $R_3$ or wherein $R_3$ is alkyl of 1–3 carbon atoms and $R_2$ is alkyl of 2–6 carbon atoms.

SYNTHESIS

These compounds may be prepared by two methods. One method follows classic peptide synthesis techniques. An ω-amino-α-amino acid is treated with appropriate protecting groups in such a way that the acid function and the α-amino group are protected but leaving the ω-amino function available for further treatment. This protected compound is then reacted with N,N'-dialkylcarbodiimide in an appropriate solvent. The reaction is carried out at temperature between about 22°–150° C. for up to about 6 hours. The solvent is then removed. In order to remove the N,N'-dialkylurea by-product, the residue is suspended in a second solvent such as dimethylformamide and the suspension filtered to recover the desired product as a solid.

Alternatively, lysine dihydrochloride or an appropriate homolog is reacted with an S-methyl-dialkyl-isothiourea.HI or a compound such as 2-methylthio-2-imidazoline.iodide in the presence of a solution of a strong base such as sodium hydroxide, potassium hydroxide or the like. The reaction is best effected at from room temperature to 90° C., preferably 60° C. over several days, i.e., 2–6 days. Additional thiourea may be added if needed after the initial reaction period. A dialkyl dicarbonate and base such as magnesium oxide are then added in an organic solvent, such as dioxane, to react with excess starting material. The reaction product is then worked up by extraction, an ion exchange resin treatment and other appropriate chromatographic means. The following examples illustrate the preparation of compounds within the scope of this invention.

PREPARATION 1

A mixture of 5.24 g of benzyl $N^\alpha$-benzyloxycarbonyl-D-lysinate toluenesulfonate (B. Bezas and L. Zervas, J. Am. Chem. Soc. 83, 719 (1961)) and 1.72 ml of diisopropylethylamine in 60 ml of dioxane is treated with 1.89 g of N,N'-diisopropylcarbodiimide. The reaction mixture is stirred at 100° C. for 6 hours, cooled to room temperature and concentrated to a solid. The solid is suspended in 20 ml of warm DMF, filtered to remove N,N'-diisopropylurea and the filtrate concentrated to a solid. Benzyl $N^\alpha$-benzyloxycarbonyl-N,N'-guanidino-diisopropyl-D-homoargininate toluenesulfonate is obtained as a white solid by crystallization from methanol/ethyl acetate $[\alpha]_D^{25}$ 4.71° (C 1, MeOH).

Similarly, by using the above procedure, but substituting:
N,N'-dimethylcarbodiimide;
N,N'-diethylcarbodiimide;
N,N'-di-n-propylcarbodiimide;
N,N'-di-i-propylcarbodiimide;
N,N'-di-n-butylcarbodiimide;
N,N'-di-i-butylcarbodiimide;
N,N'-di-n-pentylcarbodiimide;
N,N'-di-i-pentylcarbodiimide;
N,N'-dicyclohexylcarbodiimide;
N,N'-di-n-hexylcarbodiimide;
N,N'-diphenylcarbodiimide;
N,N'-ditolylcarbodiimide;
N,N'-ditolylcarbodiimide;
N-i-propylcarbodiimide;
N-propylcarbodiimide;
N,N'-bis(2,2,2-trifluoroethyl)carbodiimide;
1-(3-dimethylaminopropyl)-3-ethylcarbodiimide-HCl
and the like, there are obtained:
benzyl $N^\alpha$-benzyloxycarbonyl-N,N'-guanidino-dimethyl-D-homoargininate;
benzyl $N^\alpha$-benzyloxycarbonyl-N,N'-guanidino-diethyl-D-homoargininate, $[\alpha]_D^{25}$ 12.9° (C 0.1, MeOH);

benzyl Nα-benzyloxycarbonyl-N,N'-guanidino-di-n-propyl-D-homoargininate [α]$_D^{25}$ 10.9° (C 0.9, MeOH);

benzyl Nα-benzyloxycarbonyl-N,N'-guanidino-di-n-propyl-D-homoargininate [α]$_D^{25}$ 14.7° (C 0.4 MeOH);

benzyl Nα-benzyloxycarbonyl-N,N'-guanidino-di-n-butyl-D-homoargininate [α]$_D^{25}$ 10.7° (C 0.6, MeOH);

benzyl Nα-benzyloxycarbonyl-N,N'-guanidino-di-n-pentyl-D-homoargininate;

benzyl Nα-benzyloxycarbonyl-N,N'-guanidino-di-i-pentyl-D-homoargininate;

benzyl Nα-benzyloxycarbonyl-N,N'-guanidino-dicyclohexyl-D-homoargininate, [α]$_D^{25}$ 8.07° (C 0.9 MeOH);

benzyl Nα-benzyloxycarbonyl-N,N'-guanidino-di-n-hexyl-D-homoargininate, [α]$_D^{25}$ 10.1° (C 0.4, MeOH)

benzyl Nα-benzyloxycarbonyl-N,N'-guanidino-di-phenyl-D-homoargininate, [α]$_D^{25}$ 4.25° (C 0.4, MeOH)

benzyl Nα-benzyloxycarbonyl-N,N'-guanidino-bis(2,2,2-trifluoroethyl)-D-homoargininate;

benzyl Nα-benzyloxycarbonyl, N-guanidino-(3-dimethylaminopropyl)-N'-guanidino-ethyl-D-homoargininate [α]$_D^{25}$ 11.7° (C 0.1, MeOH) as their toluenesulfonate salts. Similiarly, by substituting benzyl Nα-benzyloxycarbonyl-D-ornithinate for the D-lysinate there may be obtained the corresponding arginine analogs as their toluenesulfonate salts.

benzyl Nα-benzyloxycarbonyl-N,N'-guanidino-di-isopropyl-D-argininate, [α]$_D^{25}$ −10.5° (C 0.5, MeOH);

PREPARATION 2

Benzyl Nα-benzyloxycarbonyl-N$^G$,N$^{G'}$-ethano-D-homoargininate

To a mixture of 15 ml of toluene and 15 ml of t-BuOH was added 2.71 g of benzyl Nα-benzyloxycarbonyl-D-lysinate and 1.46 g of 2-methylthioimidazoline.HI (available from Aldrich) or the corresponding free base obtained by partitioning the salt between methylene chloride and aqueous sodium hydroxide solution. The pH of the mixture was brought to ~8 by the addition of diisopropylethylamine and the solution heated under reflux for 24 hours.

The solution was concentrated in vacuo and the residue was loaded on a silica gel column (250 g). The column was eluted with a gradient from CH$_2$Cl$_2$/MeOH (19:1) to CH$_2$Cl$_2$/MeoH (7:3). The fractions containing product were detected by TLC, pooled, and concentrated to dryness, 2.9 g of white foam.

A 2 g portion of the above-named product was dissolved in 50 ml of EtOH containing 0.8 g of 10% Pd/C. The solution was stirred under H$_2$ for 8 hours. The mixture was filtered on celite and the filtrate was concentrated to dryness to give N$^G$,N$^{G'}$-ethano-D-homoarginine as a white foam, 1.2 g.

(ii) N$^G$,N$^{G'}$-ethano-D-homoarginine

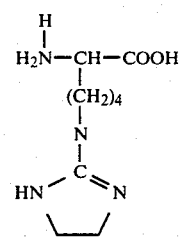

A solution of 2.74 g of D-lysine dihydrochloride and 4.03 g of 2-methylthio-2-imidazoline.hydroiodide in 16.5 ml of 2N NaOH was stirred at room temperature for 6 days. Analysis of the reaction mixture on an amino acid analyzer showed than ~70% of the desired ε-dialkylguanido compound had been formed. A further 0.25 g of the 2-methylthio-2-imidazoline.hydroiodide and 1 ml of 2N NaOH were added and the reaction was continued at room temperature for 3 more days.

The reaction mixture was treated with 0.8 g MgO and 4.36 g of di-tert-butyldicarbonate in 20 ml of dioxane. The pH was adjusted to 9.5 with 1N NaOH. After overnight reaction some starting material was present, so 1 g of di-tert-butyldicarbonate was added.

The mixture was filtered and the filtrate was concentrated to dryness. The residue was dissolved in H$_2$O and washed with Et$_2$O and the aqueous layer was adjusted to pH 4 with HOAc. The acidic solution was washed with EtOAc. The aqueous layer containing the product was treated with anion exchange resin (AG-3 acetate, BioRad) and concentrated to dryness.

The crude product was passed through a hydrophobic chromatography column (Amberlite XAD-2, Rohm & Haas) by elution with a gradient from H$_2$O to 25% EtOH. The fractions containing product were pooled to yield 2.7 g of Nα-Boc-N$^G$,N$^{G'}$-ethano-D-homoarginine as its acetate salt, [α]$_D^{25}$ −19.7° (C 0.1, MeOH).

In a similar fashion, by substituting:
S-methyl-dimethyl-iso-thiourea-HI,
S-methyl-diethyl-iso-thiourea-HI,
S-methyl-dipropyl-iso-thiourea-HI,
S-methyl-dibutyl-iso-thiourea-HI,
S-methyl-dipentyl-iso-thiourea-HI,
S-methyl-dihexyl-iso-thiourea-HI,
S-methyl-diheptyl-iso-thiourea-HI,
S-methyl-dinonyl-iso-thiourea-HI,
S-methyl-diphenyl-iso-thiourea-HI,
S-methyl,N-methyl,N'-ethyl-iso-thiourea-HI,
S-methyl,N-methyl,N'-propyl-iso-thiourea-HI,
S-methyl,N-methyl,N'-butyl-iso-thiourea-HI, and
S-methyl,N-methyl,N'-hexyl-iso-thiourea-HI
for 2-methylthio-2-imidazoline-HI, there are obtained:
S-methyl-dimethyl-iso-thiourea-HI, [α]$_D^{25}$ −19.5° (C 0.1, MeOH);
Nα-Boc-N,N'-guanidino-diethyl-D-homoarginine, [α]$_D^{25}$ −19.7° (C 0.1, MeOH);
Nα-Boc-N,N'-guanidino-dipropyl-D-homoarginine, [α]$_D^{25}$ −11.3° (C 0.5, MeOH);
Nα-Boc-N,N'-guanidino-dibutyl-D-homoarginine, [α]$_D^{25}$ −6.3° (C 0.5, MeOH)
Nα-Boc-N,N'-guanidino-dipentyl-D-homoarginine,
Nα-Boc-N,N'-guanidino-dihexyl-D-homoarginine, [α]$_D^{25}$,
Nα-Boc-N,N'-guanidino-diheptyl-D-homoarginine,
Nα-Boc-N,N'-guanidino-dinonyl-D-homoarginine, Nα-Boc-N,N'-guanidino-diphenyl-D-homoarginine,
  [α]$_D^{25}$ −9.2° (C 0.8, MeOH);
Nα-Boc-N,N'-guanidino-methyl,ethyl-D-homoarginine,
Nα-Boc-N,N'-guanidino-methyl,propyl-D-homoarginine, and
Nα-Boc-N,N'-guanidino-methyl,butyl-D-homoarginine,
Nα-Boc-N,N'-guanidino-methyl,hexyl-D-homoarginine, [α]$_D^{25}$ −2.2 (C 0.4, EtOH).

PREPARATION 3

This Preparation illustrates the preparation of N,N'-guanidino-disubstituted-D-homoarginines as their toluenesulfonate salts.

A mixture of benzyl Nα-benzyloxycarbonyl-N,N'-guanidino-diisopropyl-D-homoargininate toluenesulfonate (3.25 g) and 100 mg of 10% Pd/C in 50 ml of glacial acetic acid is treated with hydrogen gas at atmospheric pressure for 4 hours. The catalyst is filtered on celite and the filtrate is concentrated to a solid, N,N'-guanidino-diisopropyl-D-homoarginine toluenesulfonate, [α]$_D^{25}$ −3.5° (C 0.5, MeOH).

Proceeding in a similar manner, but substituting the appropriate toluenesulfonate precursors, other N,N'-guanidino-disubstituted-D-homoarginine, D-arginine as their L-analogs, or similar analogs, may be prepared, for example, the following compounds:

N,N'-guanidino-diisopropyl-D-homoarginine, [α]$_D^{25}$ −10.5° (C 0.4, MeOH);
N,N'-guanidino-di(cyclohexyl)-D-homoarginine, [α]$_D^{25}$ −7.6° (C 0.1, MeOH);
N,N'-guanidino-diphenyl-D-homoarginine, [α]$_D^{25}$ −11.7° (C 0.5, MeOH)
N,N'-guanidino-di(n-propyl)-D-homoarginine, [α]$_D^{25}$ −7.1° (C 0.4, MeOH)
N,N'-guanidino-diethyl-D-homoarginine, [α]$_D^{25}$ −6.0° (C 0.1, MeOH)
N,N'-guanidino-di(n-hexyl)-D-homoarginine, [α]$_D^{25}$ −8.3° (C 0.3, MeOH)
N,N'-guanidino-di(n-butyl)-D-homoarginine, [α]$_D^{25}$ −6.3° (C 0.5, as their toluenesulfonate salts MeOH).

What is claimed is:

1. An α-amino acid which has the formula:

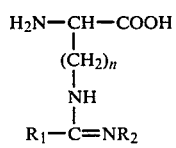

(I)

or a pharmaceutically acceptable salt thereof, wherein
  n is 1 to 5;
  R$_1$ is alkyl of 1-12 carbon atoms, halo lower alkyl or —NHR$_3$ wherein R$_3$ is alkyl of 2-6 carbon atoms, cycloalkyl, phenyl, benzyl, halo lower alkyl, morpholino or —(CH$_2$)$_n$N(R$_4$)$_2$ wheren n is 1-5 and R$_4$ is lower alkyl;
  R$_2$ is hydrogen, alkyl of 1-6 carbon atoms, cycloalkyl, phenyl, benzyl, halo lower alkyl, morpholino or —(CH$_2$)$_n$N(R$_4$)$_2$ wherein n is 1-5 and R$_4$ is lower alkyl, but is not hydrogen when R$_1$ is NHR$_3$; or
  R$_1$ and R$_2$ comprises a ring represented by one of the following structural formulas:

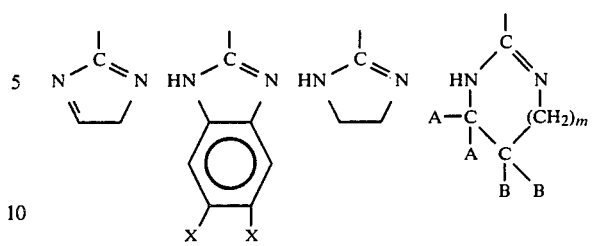

wherein
  m is 0-6;
  A and B are independently hydrogen, alkyl of 1-6 carbon atoms or cycloalkyl; and
  X is halo or A.

2. A compound of claim 1 wherein n is 3 or 4, R$_1$ is —NHR$_3$ wherein R$_3$ is alkyl of 2-6 carbon atoms and R$_2$ is alkyl of 1-6 carbon atoms, or R$_1$ and R$_2$ comprise a ring represented by one of the following structural formulas:

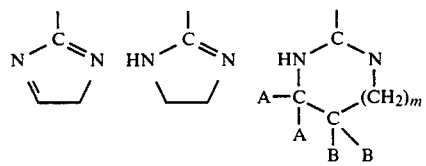

wherein m is 0-2 and A and B are hydrogen or alkyl of 1 to 4 carbon atoms, or a pharmaceutically acceptable salt thereof.

3. A compound of claim 1 wherein R$_1$ is —NHR$_3$ in which R$_3$ is alkyl of 2-6 carbon atoms or cycloalkyl, or a pharmaceutically acceptable salt thereof A.

4. A compound according to claim 3 wherein R$_1$ is —NHR$_3$ wherein R$_3$ is alkyl of 2 to 6 carbon atoms and R$_2$ is the same as R$_3$, or a pharmaceutically acceptable salt thereof.

5. A compound according to claim 4 wherein n is 4 and R$_2$ and R$_3$ are the same and are ethyl, n-propyl, n-butyl, or n-hexyl, or a pharmaceutically acceptable salt thereof.

6. A compound according to claim 5 which is N,N'-guanidino-diethylhomoarginine, or a pharmaceutically acceptable salt thereof.

7. A compound according to claim 5 which is N,N'-guanidino-dibutylhomoarginine, or a pharmaceutically acceptable salt thereof.

8. A compound according to claim 5 which is N,N'-guanidino-dipropylhomoarginine, or a pharmaceutically acceptable salt thereof.

9. A compound according to claim 3 wherein R$_1$ is —NHR$_3$ wherein R$_3$ is alkyl of 2 to 6 carbon atoms and R$_2$ is alkyl of 1 to 6 carbon atoms but is not the same as R$_3$, or a pharmaceutically acceptable salt thereof.

10. A compound according to claim 9 which is N,N'-guanidino-methyl,propylhomoarginine, or a pharmaceutically acceptable salt thereof.

11. A compound according to claim 9 which is N,N'-guanidino-methyl,butylhomoarginine, or a pharmaceutically acceptable salt thereof.

12. A compound according to claim 9 which is N,N'-guanidino-methyl,hexylhomoarginine, or a pharmaceutically acceptable salt thereof.

13. A compound according to claim 1 which is N,N'-guanidino-bis(2,2,2-trifluoroethyl)homoarginine, or a pharmaceutically acceptable salt thereof.

* * * * *